United States Patent
Farmer et al.

(10) Patent No.: US 11,278,490 B2
(45) Date of Patent: Mar. 22, 2022

(54) YEAST-BASED MASKS FOR IMPROVED SKIN, HAIR AND SCALP HEALTH

(71) Applicant: Locus IP Company, LLC, Solon, OH (US)

(72) Inventors: Sean Farmer, North Miami Beach, FL (US); Ken Alibek, Solon, OH (US)

(73) Assignee: LOCUS IP COMPANY, LLC, Solon, OH (US)

( * ) Notice: Subject to any disclaimer, the term of this patent is extended or adjusted under 35 U.S.C. 154(b) by 114 days.

(21) Appl. No.: 16/752,844

(22) Filed: Jan. 27, 2020

(65) Prior Publication Data
US 2020/0155444 A1    May 21, 2020

Related U.S. Application Data

(63) Continuation-in-part of application No. PCT/US2018/042419, filed on Jul. 17, 2018.

(60) Provisional application No. 62/538,152, filed on Jul. 28, 2017.

(51) Int. Cl.
| | |
|---|---|
| *A61K 8/9728* | (2017.01) |
| *A61K 8/24* | (2006.01) |
| *A61K 8/66* | (2006.01) |
| *A61K 8/73* | (2006.01) |
| *A61Q 5/00* | (2006.01) |
| *A61Q 19/00* | (2006.01) |

(52) U.S. Cl.
CPC ............. *A61K 8/9728* (2017.08); *A61K 8/24* (2013.01); *A61K 8/66* (2013.01); *A61K 8/737* (2013.01); *A61Q 5/00* (2013.01); *A61Q 19/00* (2013.01)

(58) Field of Classification Search
CPC ................................ A61K 8/24; A61K 8/9728
See application file for complete search history.

(56) References Cited

U.S. PATENT DOCUMENTS

| | | | |
|---|---|---|---|
| 5,981,497 A | 11/1999 | Maingault | |
| 6,057,302 A | 5/2000 | Borzeix | |
| 6,403,108 B1 | 6/2002 | Abdullah | |
| 2009/0071493 A1* | 3/2009 | Nguyen | A61Q 5/12 132/202 |
| 2011/0135616 A1* | 6/2011 | Girard | A61K 31/192 424/93.51 |
| 2014/0127257 A1 | 5/2014 | Schiemann et al. | |
| 2014/0323757 A1 | 10/2014 | Kim | |
| 2016/0083757 A1 | 3/2016 | Fonseca et al. | |
| 2017/0071842 A1 | 3/2017 | Schelges et al. | |
| 2017/0087199 A1* | 3/2017 | Patron | A61K 36/81 |
| 2017/0172913 A1* | 6/2017 | Ballesteros | A61K 8/73 |

FOREIGN PATENT DOCUMENTS

| | | |
|---|---|---|
| CN | 102078282 A | 6/2011 |
| CN | 103800224 A | 5/2014 |
| EP | 1228752 A2 | 8/2002 |
| FR | 2927254 A1 | 8/2009 |
| KR | 101608687 B1 | 4/2016 |
| RU | 2185147 C2 | 7/2002 |
| WO | 2016117489 A1 | 7/2016 |
| WO | 2018208530 A1 | 11/2018 |

OTHER PUBLICATIONS

Anonymous, "Mintel Moisturizer." Beauty Price Positioning; Prestige, Accessed from the internet on Mar. 15, 2021, [http://www.gnpd.com/sinatra/recordpage/4643835/].

Anonymous, "Mintel Reparation U.V. Soothing After-Sun Care for Face." Beauty Price Positioning; Prestige, Accessed from the internet on Mar. 15, 2021, [http://www.gnpd.com/sinatra/recordpage/3274251/].

De Almeida, D., et al., "Biosurfactants: Promising Molecules for Petroleum Biotechnology Advances." Frontiers in Microbiology, Oct. 2016, 7(1718): 1-14.

De Brito, D., Biosurfactants from renewable raw materials, Universidade do Minho Departamento de Engenharia Biologica, Nov. 2013, pp. 1-93.

De Oliveira, M., et al., "Review: Sophorolipids A Promising Biosurfactant and it's Applications." International Journal of Advanced Biotechnology and Research, 2015, 6(2): 161-174.

Gharaei-Fathabad, E., "Biosurfactants in Pharmaceutical Industry (A Mini-Review)." American Journal of Drug Discovery and Development, 2011, 1(1): 58-69.

Meena, K.R., et al., "Lipopeptides as the Antifungal and Antibacterial Agents: Applications in Food Safety and Therapeutics." BioMed Research International, 2015, 2015: Article ID 473050, 1-9.

Sen, R., "Biosurfactants: Advances in Experimental Medicine and Biology." Landes Bioscience and Springer Science+Business Media, LLC, 2010, 672: 1-331.

Sharma, A. et al., "A study on biosurfactant production in *Lactobacillus* and *Bacillus* sp." Int. J. Curr. Microbiol. App. Sci., 2014, 3(11): 723-733.

(Continued)

*Primary Examiner* — Benjamin J Packard

(74) *Attorney, Agent, or Firm* — Saliwanchik, Lloyd & Eisenschenk

(57) ABSTRACT

The subject invention provides materials and methods for improving facial skin, hair and scalp health using cosmetic yeast-based masks. In a specific embodiment, the subject invention provides a yeast-based mask for application to the face, which can improve the health and appearance of thereof. In another specific embodiment, the subject invention provides a yeast-based mask for application to the hair and scalp, which can aid in preventing hair loss, as well as improve the health and appearance of the hair and scalp. Methods of using the yeast-based masks are also provided.

32 Claims, No Drawings

(56) References Cited

OTHER PUBLICATIONS

Shen, C., et al., "Targeted killing of myofibroblasts by biosurfactant di-rhamnolipid suggests a therapy against scar formation." Scientific Reports, 2016, 6(1): 1-10.

* cited by examiner

YEAST-BASED MASKS FOR IMPROVED SKIN, HAIR AND SCALP HEALTH

CROSS-REFERENCE TO RELATED APPLICATIONS

This application is a continuation-in-part (CIP) application of International Application No. PCT/US2018/042419, filed Jul. 17, 2018, which claims the benefit of U.S. Provisional Patent Application No. 62/538,152, filed Jul. 28, 2017, which is incorporated herein by reference in its entirety.

BACKGROUND OF THE INVENTION

Cosmetics and the enhancement of physical appearance have been a part of daily life for humans for decades. Of all cosmetic beauty concerns, the enhancement of facial skin health and appearance is one of the most desirable. The selective treatment of the face is thus of great importance to consumers. There are a variety of cosmetic delivery systems, such as lotions, scrubs, washes, tonics, creams, sprays, splashes, gels, and sticks that have been used to provide beneficial ingredients and compositions to facial areas. Cosmetic masks, in particular, are some of the most popular and convenient delivery systems available.

Various mask products for application to the face, chin, neck and ears can be formulated to deliver specific benefits for the skin of those areas. These benefits include compounds for aging, wrinkle reduction, acne treatment, toning, lightening, tightening, moisturizing, smoothing, exfoliating, and many others. Moreover, masks can be applied to site-specific locations of the human body for maximum absorption, bioavailability, and overall benefit to the skin. Furthermore, masks can adsorb to the skin and remove unwanted oils, pollutants, impurities, bacteria, and dead cells therefrom. Additional deep cleansing of the facial skin can occur upon removal of a mask, for example after it has dried on the face and is peeled or washed away.

One emerging trend in the field of cosmetic skin improvement masks is the use of microorganisms in the mask formulation. *Saccharomyces* yeasts are considered a natural source of health, beauty and youthfulness for their ability to regenerate and moisturize the skin, promote improved blood circulation and metabolism, and protect skin from the effects of free radicals. Yeast have been used for decades in homemade skin improvement remedies due to a rich combination of active components. In particular, yeasts can provide amino acids and peptides to enhance substances that take part in the removal of toxins, slow the process of pigmentation and activate the mechanism of collagen production.

Furthermore, yeasts provide certain vitamins that are essential for skin health, including: B1 (thiamine), for regulation of carbohydrate, fat, and protein metabolism, energy, and water-salt balance, as well as combating premature skin aging; B2 (riboflavin), which plays an important role in oxidation-reduction reactions, the synthesis of other vitamins in the body and improves coloration and shading of the face; B3 (nicotinamide, niacin), which has vasodilating properties and promotes the conversion of fats and sugars to energy; B5 (pantothenic acid), which helps in the production of antibodies for increasing immune defense, for example, against viral infections; Biotin (B7 or H), which helps in carrying carbon dioxide through the circulatory system, participates in the maxim of glucokinase and is necessary for activation of ascorbic acid, which is important for stimulating skin cell regeneration; B9 (folic acid), which is indispensable in the production of red blood cells, affects the development and growth of all tissues, effectively stops the spread of acne and blocks repeated rashes; and vitamin E (tocopherol), which is a strong antioxidant that can protect cell membranes from the negative effects of free radicals and prevent the mechanism of pathological peroxidation, thereby fighting the aging process.

Yeasts can also provide various macro- and microelements (e.g., sodium, phosphorus, potassium, iron, calcium, iodine, magnesium, molybdenum, zinc and other minerals) actively involved in metabolism, as well as in reducing inflammatory processes, rejuvenating the skin and controlling sebaceous glands' secretion of subcutaneous fat.

Another area of cosmetics for which yeast compositions can be useful is hair and scalp health. Hair loss is a common problem and is caused by weakening of the hair follicles, poor oxygenation, accumulation of free radicals and certain deficiencies in essential nutrients. There are various treatments designed to fight hair loss and improve the health of the scalp to stimulate hair growth. These include, for example, hair transplantation, drug and hormone therapy, and non-drug therapies, such as UV radiation, exercise therapy, revascularization surgery and acupuncture. Some commercial products, for example shampoos and exfoliants, are either ineffective, or are expensive for permanent use.

Yeast-based products, however, have shown promising results as cost-effective alternatives for treating hair loss and improving scalp health. Most known applications for hair and scalp health involve the use of brewer's or baker's yeast (*Saccharomyces*). The same vitamins, minerals and proteins provided by the yeasts that are beneficial for facial skin health can also help with strengthening of hair follicles, promoting growth of hair, and preventing hair loss. However, these types of yeasts are ineffective at controlling pathogenic fungi and bacteria that might also lead to conditions such as alopecia, hair thinning and dandruff.

The cosmetic industry is a multi-billion dollar industry that provides products to consumers that can enhance health and physical appearance; however, many cosmetics can comprise certain ingredients that are harmful to humans and/or the environment, and furthermore, many cosmetic products are simply ineffective for their purported purpose. Thus, there are continuing needs for cosmetic products that are economical, safe, and effective for consumers. Of particular need are compositions and methods for improving the health and appearance of facial skin, scalp and hair.

BRIEF SUMMARY OF THE INVENTION

The present invention provides microbe-based products, as well as methods of their production and use, in topical cosmetic compositions. More specifically, the present invention provides materials and methods for improving skin, hair and scalp health, using topical cosmetic compositions comprising microbe-based products. Advantageously, the topical compositions and methods of the subject invention are environmentally-friendly, non-pharmaceutical, and cost-effective.

In preferred embodiments, topical cosmetic compositions are provided comprising therapeutically-effective amounts of microorganisms and/or their growth by-products.

In one embodiment, the topical cosmetic composition is formulated as a facial mask for improving facial skin. In preferred embodiments, the facial mask is a peel-off mask. The mask can also be formulated as a wash-off mask or a paper mask.

In one embodiment, the topical cosmetic composition is formulated as a hair mask for improving scalp and hair health.

In one embodiment, the composition can comprise therapeutically-effective amounts of live or inactive yeast cells and/or growth by-products thereof. Further ingredients such as, for example, plant-based oils, sodium alginate, xanthan gum, calcium sulfate dihydrate, sorbitol, magnesium oxide, guar gum, diatomaceous earth, tetrasodium pyrophosphate, one or more skin active agents, and water, can also be included. The composition can further comprise yeast extract (e.g., *Saccharomyces* yeast hydrolysate and/or autolysate).

In some embodiments, the composition for improving skin, hair and scalp health further comprises one or more biosurfactants produced by microorganisms. Specifically, in certain embodiments, the compositions can comprise a therapeutically effective amount of glycolipids (e.g., mannosylerythritol lipids (MELs), sophorolipids (SLPs), rhamnolipids (RLPs), trehalose lipids (TLs)), lipopeptides (e.g., surfactin, lichenysin, iturin or fengycin), or a combination thereof. The biosurfactants can be purified, or the biosurfactants can be used in crude form, meaning they are not separated from the fermentation broth in which they were produced.

In some embodiments, the topical composition further comprises therapeutically effective amounts of one or more additional skin active agents for, e.g., replenishing, rejuvenating, moisturizing, protecting and/or improving the appearance and/or health of the skin, hair and/or scalp in any way (e.g., phosphatidylglycerol, resveratrol, hyaluronic acid, anti-fungals, or anti-comedo agents).

In certain preferred embodiments, the topical composition comprises about 0.01 to about 1.0 g/L of phosphatidylglycerol.

In some embodiments, the topical composition can further comprise a topically acceptable vehicle, such as a water-in-oil or oil-in-water emulsion, or an aqueous serum.

In some embodiments, the topical cosmetic composition can further comprise additional adjuvants and additives typically found in cosmetic compositions, such as, for example, organic solvents, silicones, antimicrobials, stabilizers, thickeners, softeners, sunscreens, moisturizers, conditioners or fragrances.

In certain embodiments, methods are provided for improving the health and/or appearance of a subject's facial skin, the methods comprising:
  a) cleaning the subject's facial skin using a non-medicated cleanser to remove makeup, dirt and oil from the skin;
  b) producing a facial mask composition comprising yeast cells and/or growth by-products thereof; c) applying a thin layer of the facial mask composition to the facial skin; d) allowing the facial mask composition to dry on the skin for a number of minutes; and e) washing away the facial mask composition using warm water.

In one embodiment, step b) can comprise adding yeast cells to a plant-based oil such as coconut oil or olive oil and mixing with water to form a thick paste. For example, in one embodiment, step b) can comprise mixing approximately 30-50 g of yeast cells with a natural oil, such as olive oil or coconut oil.

In some specific embodiments, the method comprises:
  a) cleaning the subject's facial skin using a non-medicated cleanser to remove makeup, dirt and oil from the skin; b) producing a peel-off facial mask composition comprising yeast cells and/or growth by-products thereof; c) applying a thin layer of the facial mask composition to the facial skin; d) allowing the facial mask composition to dry on the skin for a number of minutes to form a compact film; and e) peeling the film from the skin; and f) washing away any remaining film on the skin using warm water.

In some embodiments, step b) can comprise adding yeast cells to a powder mixture comprising sodium alginate, xanthan gum, calcium sulfate dihydrate, sorbitol, magnesium oxide, guar gum, diatomaceous earth, and tetrasodium pyrophosphate to form a yeast-powder mixture; and mixing the yeast-powder mixture with water at a ratio of, for example, about 1:25 to create a liquid or semi-liquid facial mask composition.

Step b) of the subject methods for improving the health and/or appearance of facial skin can further comprise adding other ingredients or suitable additives and/or adjuvants to the composition, for example, a microbial biosurfactant or a skin-active agent, such as, e.g., phosphatidylglycerol.

The method can be applied once or twice daily, for as many days, weeks, or months as necessary for the subject to achieve the desired improvement, replenishment, rejuvenation, moisturization and/or protection of the facial skin, which can include, for example, more even skin tone, more radiant skin appearance, softer skin, reduction in redness, reduction in wrinkles, and/or reduction in pore size. The method can further be used for treating a skin condition, for example, acne vulgaris and/or others described herein.

In certain embodiments, the subject invention provides methods for improving hair and scalp health, the methods comprising applying an effective amount of the topical cosmetic composition directly to the scalp and hair for a number of minutes sufficient to achieve a desired amount of improvement in hair and/or scalp health and/or appearance.

In one embodiment, the method for improving hair and scalp health comprises: a) mixing approximately 30-50 g of yeast cells with olive oil or coconut oil to form a yeast-oil mixture; b) adding water to the yeast-oil mixture to form a thick paste; c) applying the paste to a subject's dry hair and scalp; d) covering the subject's hair with plastic wrap; e) allowing the paste to sit on the hair and scalp for at least 60 minutes, and f) rinsing the paste from the hair and scalp using water.

Steps a) and/or b) of the methods for improving hair and scalp health can further comprise adding other ingredients or suitable additives and/or adjuvants to the composition, for example, a microbial biosurfactant or a skin-active agent, e.g., phosphatidylglycerol.

The method can be applied once or twice daily, for as many days, weeks, or months as necessary for the subject to achieve the desired improvements in the health and/or appearance of the hair and/or scalp.

The method can further be used for treating a scalp condition, for example, dandruff or alopecia. For such uses, the topical composition is applied directly to an area where such a condition exists for a time sufficient to alleviate or reduce the symptoms of the condition.

As described, the compositions of the subject invention comprise yeast cells, which may be included in the composition as live cells or inactive cells. The terms "yeast extract," and/or *Saccharomyces* hydrolysate or autolysate are not included when reference is made to "yeast cells."

Preferably, the yeast cells are capable of producing one or more desirable growth by-products, such as, for example, biosurfactants, enzymes and proteins. In some embodiments, the yeasts are *Pichia* clade yeasts, selected from *P. anomala* (*Wickerhamomyces anomalus*), *P. kudriavzevii* (*Wickerhamomyces kudriavzevii*), and/or *P. guilliermondii* (*Meyerozyma guilliermondii*). In some embodiments, the yeasts are biochemical-producing yeasts, for example, yeasts capable of producing glycolipid biosurfactants, such as, e.g., *Starmerella, Pseudozyma*, and others.

In further embodiments, the subject invention comprises kits for at-home preparation and use of the subject compositions for enhancing skin, hair and scalp health and appearance.

DETAILED DESCRIPTION OF THE INVENTION

The present invention provides materials and methods for improving skin, hair and scalp health, using topical cosmetic compositions that comprise biochemical-producing yeasts and/or their growth by-products. Advantageously, the topical compositions and methods of the subject invention are environmentally-friendly, non-pharmaceutical, and cost-effective.

In preferred embodiments, the composition comprises therapeutically-effective amounts of yeast cells and/or growth by-products thereof. The composition can further comprise one or more other ingredients, such as, for example, a plant-based oil, sodium alginate, xanthan gum, calcium sulfate dihydrate, sorbitol, magnesium oxide, guar gum, diatomaceous earth, tetrasodium pyrophosphate, water and/or one or more skin-active agents. The composition can further comprise yeast extract (e.g., *Saccharomyces* yeast hydrolysate or autolysate).

In one embodiment, the topical cosmetic composition is formulated as a facial mask for improving facial skin. In preferred embodiments, the facial mask is a peel-off mask. The mask can also be formulated as a wash-off mask or a paper mask.

In one embodiment, the topical cosmetic composition is formulated as a hair mask for improving scalp and hair health.

As described, the compositions of the subject invention comprise yeast cells, which may be included in the composition as live cells or inactive cells. The terms "yeast extract," and/or *Saccharomyces* hydrolysate or autolysate are not included when reference is made to "yeast cells."

Preferably, the yeast cells are capable of producing one or more desirable growth by-products, such as, for example, biosurfactants, enzymes and/or proteins. In some embodiments, the yeasts are *Pichia* clade yeasts, such as, for example, *P. anomala* (*Wickerhamomyces anomalus*), *P. kudriavzevii* (*Wickerhamomyces kudriavzevii*), and/or *P. guilliermondii* (*Meyerozyma guilliermondii*). In some embodiments, the yeasts are capable of producing glycolipid biosurfactants (e.g., *Starmerella, Pseudozyma*, and others).

In certain preferred embodiments, the composition further comprises a skin-active agent, such as a microbial biosurfactant and/or phosphatidylglycerol.

The subject invention further provides at-home kits for preparation and use of the subject compositions for enhancing skin, scalp and hair health and appearance.

Selected Definitions

As used herein, a "microbe-based composition" means a composition that comprises components that were produced as the result of the growth of microorganisms or other cell cultures. Thus, the microbe-based composition may comprise the microbes themselves and/or by-products of microbial growth (e.g., biosurfactants, solvents and/or enzymes). The cells may be in a vegetative state or in spore form, or a mixture of both. The cells may be planktonic or in a biofilm form, or a mixture of both. The cells may be intact or lysed. The cells can be present, with broth in which they were grown, at, for example, a concentration of $1 \times 10^4$, $1 \times 10^5$, $1 \times 10^6$, $1 \times 10^7$, $1 \times 10^8$, $1 \times 10^9$, $1 \times 10^{10}$, or $1 \times 10^{11}$ or more cells per milliliter of the composition. In one embodiment, the microbe-based composition may comprise only the broth in which the cells were grown, with the cells removed. The by-products of growth may be present in the broth and can include, for example, metabolites, cell membrane components, expressed proteins, and/or other cellular components.

The subject invention further provides "microbe-based products," which are products that are to be applied in practice to achieve a desired result. The microbe-based product can be simply the microbe-based composition harvested from the microbe cultivation process. Alternatively, the microbe-based product may comprise further ingredients that have been added. These additional ingredients can include, for example, stabilizers, buffers, appropriate carriers, such as water, salt solutions, or any other appropriate carrier, added nutrients to support further microbial growth, non-nutrient growth enhancers, and/or agents that facilitate tracking of the microbes and/or the composition in the environment to which it is applied. The microbe-based product may also comprise mixtures of microbe-based compositions. The microbe-based product may also comprise one or more components of a microbe-based composition that have been processed in some way such as, but not limited to, filtering, centrifugation, lysing, drying, purification and the like.

A "metabolite" refers to any substance produced by metabolism (e.g., a growth by-product) or a substance necessary for taking part in a particular metabolic process. A metabolite can be an organic compound that is a starting material (e.g., glucose), an intermediate (e.g., acetyl-CoA) in, or an end product (e.g., n-butanol) of metabolism. Examples of metabolites can include, but are not limited to, enzymes, acids, solvents, alcohols, proteins, carbohydrates, vitamins, minerals, microelements, amino acids, polymers, and biosurfactants.

As used herein, the terms "isolated" or "purified," when used in connection with biological or natural materials such as nucleic acid molecules, polynucleotides, polypeptides, proteins, organic compounds, such as small molecules, microorganism cells/strains, or host cells, means the material is substantially free of other compounds, such as cellular material, with which it is associated in nature. That is, the materials do not occur naturally without these other compounds and/or have different or distinctive characteristics compared with those found in the native material.

In certain embodiments, purified compounds are at least 60% by weight the compound of interest. Preferably, the preparation is at least 75%, more preferably at least 90%, and most preferably at least 99% or 100% (w/w) of the desired compound by weight. Purity is measured by any appropriate standard method, for example, by column chromatography, thin layer chromatography, or high-performance liquid chromatography (HPLC) analysis.

As used herein, "surfactant" means a surface-active substance that lowers the surface tension (or interfacial tension) between two liquids or between a liquid and a solid. Surfactants act as, for example, detergents, wetting agents, emulsifiers, foaming agents, and/or dispersants. By "biosurfactant" is meant a surface-active substance produced by a living cell.

As used herein, the term "subject" refers to an animal, especially a mammal. In preferred embodiments, the subject is a human of any gender. The subject can be of any age or stage of development including infant, toddler, preteen, adolescent, teenager, adult and senior.

As used herein, "cosmetically-acceptable," "topically-acceptable" and "dermatologically-acceptable" are used interchangeably and are intended to mean that a particular component is safe and non-toxic for application to a human integument (e.g., skin) at the levels employed. In one embodiment, the components of the composition are recognized as being Generally Regarded as Safe (GRAS).

As used herein the terms "improving," "enhancing" and "replenishing," when used in the context of the skin (including facial skin), scalp and hair, include providing a benefit to or a positive change in the skin, scalp and/or hair. Such a change can be a benefit to or positive change in the appearance of the skin, scalp and/or hair, as well as the health of the skin, scalp and/or hair. The benefit or positive change can be permanent or temporary. In certain exemplary embodiments, the benefit provided to skin can include, for example, more even skin tone, more radiant skin appearance, softer skin, reduction in redness, reduction in wrinkles, and/or reduction in pore size.

"Improving" can also include the treatment of any condition of the skin, scalp or hair. As used herein, the term "treatment" refers to eradicating, reducing, alleviating, ameliorating, or reversing, a sign or symptom of a condition or disorder to any extent, and includes, but does not require, a complete cure of the condition or disorder. Thus, treating can include curing or partially reducing or ameliorating a disorder.

As used herein, "preventing" a condition or disorder refers to avoiding, delaying, forestalling, or minimizing the onset of a particular sign or symptom of the condition or disorder. Prevention can, but is not required to be, absolute or complete, meaning the sign or symptom may still develop at a later time. Prevention can include reducing the severity of the onset of such a condition or disorder, and/or inhibiting the progression of the condition or disorder to a more severe condition or disorder.

As used herein, the terms "therapeutically effective amount," "therapeutically effective dose," "effective amount," and "effective dose" are used to refer to an amount of something (e.g., a compound, a composition, time) that is capable of treating or preventing a condition or disorder in a subject. The actual amount will vary depending on a number of factors including, but not limited to, the particular condition or disorder, the severity of the condition or disorder, the size, age, and health of the subject, and the route of administration.

As used herein, the term "skin condition" encompasses human and animal conditions, disorders, or diseases affecting skin. Such skin conditions include, but are not limited to, conditions involving the epidermis, dermis (including connective tissue, sebaceous glands and hair follicles), and the subcutaneous tissue (hypodermis). Symptoms of skin conditions can include, for example, acneiform symptoms, pigmentation or loss thereof, redness, flushing, inflammation, wrinkles, dryness, looseness, thickening, scaling, scarring, flaking, uneven skin tone, rash, hives, blisters, ulcers, peeling, hair loss, enlarged pores, and other changes in the appearance of the skin. Skin conditions that can, in certain embodiments, be treated and/or preventing using compositions, products and methods described herein include, but are not limited to, acne, blemishes, rosacea, folliculitis, carcinoma, melanoma, perioral dermatitis, cellulitis, carbuncles, photodamage, skin aging (e.g., wrinkles and dryness), age spots, scars, lupus, psoriasis, ichtiosis, atopic dermatitis, chronic wounds, bed sores, keratosis piralis, sebaceous cysts, vitiligo, melisma, warts, inflammatory dermatoses, post inflammatory hyperpigmentation, keratoses, eczema, xerosis, pruritis, lichen planus, nodular prurigo, microbial infection, body odor and miliaria. In some embodiments, a symptom of a skin condition can also be a skin condition itself.

As used herein, the terms "scalp condition" and "hair condition" encompass human and animal conditions, disorders, or diseases affecting the scalp and/or the hair. Such conditions include, but are not limited to, dry hair or scalp, thinning hair, brittle hair, hair loss, male pattern baldness, alopecia, ringworm, seborrheic eczema, seborrheic dermatitis, cradle cap, acne, psoriasis, head lice, tricorrhexis nodosa, dandruff, for example, that caused by *Malassezia* fungi, folliculitis caused by, for example, *Staphylococcus aureus*, and others.

The transitional term "comprising," which is synonymous with "including," or "containing," is inclusive or open-ended and does not exclude additional, unrecited elements or method steps. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention.

Unless specifically stated or obvious from context, as used herein, the term "or" is understood to be inclusive. Unless specifically stated or obvious from context, as used herein, the terms "a," "an" and "the" are understood to be singular or plural.

Unless specifically stated or obvious from context, as used herein, the term "about" is understood as within a range of normal tolerance in the art, for example, within 2 standard deviations of the mean. "About" can be understood as within 10%, 9%, 8%, 7%, 6%, 5%, 4%, 3%, 2%, 1%, 0.5%, 0.1%, 0.05%, or 0.01% of the stated value.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

Other features and advantages of the invention will be apparent from the following description of the preferred embodiments thereof, and from the claims. All references cited herein are hereby incorporated by reference.

Cosmetic Compositions for Improving Skin, Scalp and Hair Health

The present invention provides topical cosmetic compositions for improving skin, scalp and/or hair health, wherein the compositions comprise therapeutically-effective amounts of cultivated microorganisms and/or their growth by-products. Preferably, the cosmetic compositions are in the form of a facial mask or a hair mask. In one embodiment, the compositions comprise from 10% to 50% w/w yeast cells, more preferably from 20% to 40%, even more preferably, 30% w/w.

A "facial mask" or "face mask" is a composition applied to the face and/or neck and left thereon for a certain period of time before removing. Facial masks can comprise ingredients to revitalize, replenish, heal, refresh or provide some other benefit or treatment to the skin of the face, whether temporary or permanent. Some masks are designed to dry or solidify on the face, while others remain wet or in gel-form. Masks can be removed by rinsing with water, wiping with a cloth, or peeling from the face.

A "hair mask" refers to a conditioning and strengthening treatment for the hair and/or scalp that is applied to the hair and scalp and left thereon for a certain period of time before removing (e.g., rinsing with water). Typically, hair masks can contain deeply conditioning and moisturizing ingredients, as well as oils or extracts, strengthening proteins, vitamins, and other beneficial ingredients. Hair masks can be useful for people with any type of hair, e.g., oily to dry to color-treated.

In one embodiment, the composition can comprise therapeutically-effective amounts of live or inactive yeast cells and/or growth by-products thereof. Further ingredients such as, for example, plant-based oils, sodium alginate, xanthan gum, calcium sulfate dihydrate, sorbitol, magnesium oxide, guar gum, diatomaceous earth, tetrasodium pyrophosphate, water, and/or one or more skin-active agents, can also be included. The composition can further comprise yeast extract (e.g., *Saccharomyces* yeast hydrolysate and/or autolysate), in addition to the yeast cells.

In some embodiments, the composition for improving skin, hair and scalp health further comprises one or more biosurfactants produced by microorganisms. Specifically, in certain embodiments, the compositions can comprise a therapeutically effective amount of glycolipids (e.g., mannosylerythritol lipids (MELs), sophorolipids (SLPs), rhamnolipids (RLPs), trehalose lipids (TLs)), lipopeptides (e.g., surfactin, lichenysin, iturin or fengycin), or a combination thereof. The biosurfactants can be purified, or the biosurfactants can be used in crude form, meaning they are not separated from the fermentation broth in which they were cultivated.

In some embodiments, the topical composition further comprises therapeutically effective amounts of one or more skin-active agents for, e.g., replenishing, rejuvenating, moisturizing, protecting and/or improving the appearance and/or health of the skin, hair and/or scalp in any way (e.g., phosphatidylglycerol, resveratrol, hyaluronic acid, anti-fungals, and/or anti-comedo agents).

In one embodiment, the topical cosmetic composition is formulated as a face mask for improving and/or replenishing facial skin, for example, by leveling the skin relief, smoothing wrinkles, reducing age spots, reducing redness, eliminating excessive shine, reducing inflammation, purifying and reducing the size of pores, restoring skin's natural color, softening the skin, and increasing the turgor, fullness, elasticity and overall radiance of skin.

In preferred embodiments, the composition for improving facial skin is formulated as a peel-off mask. The mask can also be formulated as a wash-off mask or even a paper mask.

In a specific embodiment, the composition for improving facial skin comprises therapeutically effective amounts of yeast cells and/or growth by-products thereof, and one or more of the following: a plant-based oil, sodium alginate, xanthan gum, guar gum, calcium sulfate dihydrate, sorbitol, magnesium oxide, diatomaceous earth, tetrasodium pyrophosphate, water and/or one or more skin-active agents. The amounts of these ingredients can be adjusted depending upon, for example, the amount of facial skin to be covered and the particular improvement to the facial skin that is desired.

In an exemplary embodiment, one application of the facial mask composition can comprise 20-70 g of yeast cells, more preferably from 30 to 50 g; and about 50 ml to 300 ml of a plant-based oil, such as, e.g., coconut oil, olive oil, jojoba oil, rose hip seed oil, vegetable oil, argan oil, or avocado oil).

In an exemplary embodiment, the face mask composition can be formulated as a peel-off mask comprising 30% w/w yeast cells; 5.0% to 15.0% w/w sodium alginate, preferably 10.0% w/w; 1.0% to 5.0% xanthan gum, preferably 2.0% w/w; 1.0% to 20% w/w, calcium sulfate dihydrate, preferably 10.0% w/w; 1.0% to 20% w/w sorbitol, preferably 10.0% w/w; 1.0% to 10.0% w/w magnesium oxide, preferably 4.5% w/w; 1.0% to 5.0% w/w guar gum, preferably 2.0% w/w; 10.0% to 50.0% w/w diatomaceous earth, preferably 30.0% w/w; and 0.5% to 5.0% w/w tetrasodium pyrophosphate, preferably 1.5% w/w.

If yeast extract is included, about 5 to about 25 g are added, more preferably about 5 to 15 g.

In some embodiments, the topical cosmetic composition is formulated as a hair mask that can be used for improving scalp and hair health.

For example, the hair mask composition can comprise therapeutically-effective amounts of yeast cells and/or growth by-products thereof, and a natural oil (e.g., a plant-based oil such as olive oil, coconut oil, jojoba oil, rose hip seed oil, argan oil, or avocado oil). The composition can further comprise yeast extract (e.g., *Saccharomyces* yeast autolysates) and/or cosmetic additives, such as a natural hair colorant.

In an exemplary embodiment, one application of the mask composition comprises 20-70 g of yeast cells, more preferably from 30 to 50 g; and about 50 ml to 300 ml of oil.

If yeast extract is included, about 5 to about 25 g are added, more preferably about 5 to 15 g.

The amounts of each ingredient can be adjusted depending upon, for example, the amount of hair and/or scalp to be covered and the particular improvement to the hair and/or scalp that is desired.

In preferred embodiments, the compositions of the subject invention comprise microorganisms and/or their growth by-products. The microorganisms can be, for example, bacteria, yeast and/or fungi. These microorganisms may be natural, or genetically modified microorganisms. For example, the microorganisms may be transformed with specific genes to exhibit specific characteristics. The microorganisms may also be mutants of a desired strain. As used herein, "mutant" means a strain, genetic variant or subtype of a reference microorganism, wherein the mutant has one or more genetic variations (e.g., a point mutation, missense mutation, nonsense mutation, deletion, duplication, frameshift mutation or repeat expansion) as compared to the reference microorganism. Procedures for making mutants are well known in the microbiological art. For example, UV mutagenesis and nitrosoguanidine are used extensively toward this end.

In preferred embodiments, the microorganism is a yeast or fungus. Yeast and fungus species suitable for use according to the current invention, include *Acaulospora, Aspergillus, Aureobasidium* (e.g., *A. pullulans*), *Blakeslea, Candida* (e.g., *C. albicans, C. apicola*), *Debaryomyces* (e.g., *D. hansenii*), *Entomophthora, Fusarium, Hanseniaspora* (e.g., *H. uvarum*), *Hansenula, Issatchenkia, Kluyveromyces, Mortierella, Mucor* (e.g., *M. piriformis*), *Penicillium, Phythium, Phycomyces, Pichia* (e.g., *P. anomala, P. guielliermondii, P. occidentalis, P. kudriavzevii*), *Pseudozyma* (e.g., *P. aphidis*), *Rhizopus, Saccharomyces* (*S. cerevisiae, S. boulardii sequela, S. torula*), *Starmerella* (e.g., *S. bombicola*), *Torulopsis, Thraustochytrium, Trichoderma* (e.g., *T. reesei, T.*

*harzianum, T virens), Ustilago* (e.g., *U. maydis*), *Wickerhamomyces* (e.g., *W. anomalus*), *Williopsis* and/or *Zygosaccharomyces* (e.g., *Z. bailii*).

Ever more preferably, the microorganism is a yeast known as a "killer yeast." As used herein, "killer yeast" means a strain of yeast characterized by its secretion of toxic proteins or glycoproteins, to which the strain itself is immune. The exotoxins secreted by killer yeasts are capable of controlling other strains of yeast, fungi, or bacteria. For example, microorganisms that can be controlled by killer yeast include *Fusarium* and other filamentous fungi. Such yeasts can include, but are not limited to, *Wickerhamomyces, Pichia, Hansenula, Hanseniaspora, Ustilago Debaryomyces, Candida, Cryptococcus, Kluyveromyces, Torulopsis, Williopsis, Zygosaccharomyces* and others.

In specific embodiments, the microbes are *Pichia* clade yeasts, including *Pichia anomala* (*Wickerhamomyces anomalus*), *P. kudriavzevii* (*Wickerhamomyces kudriavzevii*) *P. guilliermondii* (*Meyerozyma guilliermondii*), and/or combinations thereof.

The microorganisms can be used in a live, inactive and/or dried cell form. These species of yeast are especially advantageous for use in the subject invention due to their superiority over *Saccharomyces* yeasts. For example, these species produce hydrolytic enzymes capable of destroying microbial cell walls.

Additional advantages to the use of *Pichia* yeasts is that they are non-pathogenic to humans, as evidenced by their use in various areas of the food industry. Furthermore, these strains of yeast and their derivatives do not cause negative side effects on human skin and mucosa (unless, of course, the subject has a yeast allergy).

Specific benefits to use of *Pichia anomala* include its production of a broad-spectrum antifungal/antibacterial toxin, exo-beta-1,3-glucanase, which is capable of killing many fungi of human skin and mucosa. Moreover, this yeast's toxin shows antifungal activity against skin, mouth, bladder and *Candida* spp. isolates. This yeast strain can also produce phospholipids and enzymes, including esterases, lipases, glycosidases, amylases, and proteases that can be beneficial for improving the quality of skin.

*Pichia kudriavzevii* produces a protein that can suppress certain pathogens that are significant to human health, e.g., *Escherichia coli, Enterococcus faecalis, Klebsiella* spp, *Staphylococcus aureus, Pseudomonas aeruginosa, Pseudomonas alcaligenes* and *Propionibacterium acnes.*

*Pichia guilliermondii* produces the enzyme chitinase, which has significant capacity for killing fungi, including *Malassezia*, a cause and/or promoter of psoriasis, eczema, atopic dermatitis, dandruff, dry skin, Tinea Versicolor, rosacea, seborrheic dermatitis, and fungal acnes.

In certain embodiments, the compositions of the subject invention comprise microbial growth by-products, for example, biological amphiphilic molecules (e.g., biosurfactants) produced by the cultivation of biochemical-producing microorganisms. In some embodiments, the biological amphiphilic molecules are utilized in a crude form, wherein the molecule is present in the broth in which the microorganism is cultivated and is collected therefrom without purification. The crude form can comprise, for example, at least 20%, 30%, 40%, 50%, 60%, 70% or 80% amphiphilic molecule in broth. In some embodiments, the biological amphiphilic molecules have been purified from the products of cultivation.

In certain embodiments, the composition can comprise a therapeutically effective amount of glycolipids, such as mannosylerythritol lipids (MELs), sophorolipids (SLPs), trehalose lipids (TLs) and rhamnolipids (RLP); and/or lipopeptides, such as surfactin, iturin A, and fengycin. In one embodiment, the composition can comprise a combination of any of these biosurfactants.

The biological amphiphilic molecules according to the present invention are capable of one or more of the following: killing pathogenic agents in the skin, modulating the skin's immune system, killing melanocytes to allow for replacement cells to grow, reducing oxidative stress, enhancing multiplication and function of keratinocytes and fibroblasts, and enhancing dermal penetration of both the e.g., biosurfactants, and one or more other active ingredients in the composition. Thus, while providing therapeutic benefits themselves, these beneficial molecules can also enhance the overall effectiveness of the topical composition in treating skin, scalp and/or hair conditions related to, for example, the presence of microbial agents.

MELs are glycolipids produced mainly by the yeast genus *Pseudozyma*. MELs are non-toxic and are stable at wide temperatures and pH ranges. Furthermore, MELs can be used without any additional preservatives.

In preferred embodiments, MEL concentration in the topical cosmetic composition ranges from 0.001% to 90% of the total composition by weight, from 0.01% to 50%, from 0.05% to 10%, and preferably from 0.1% to 2.0%.

SLPs are produced in large quantity by several nonpathogenic yeast species, the most studied of which is *Starmerella bombicola*. Some *Pichia* yeasts (e.g., *P. anomala*) are also capable of producing SLPs. SLPs have environmental compatibility, high biodegradability, low toxicity, high selectivity and specific activity in a broad range of temperature, pH and salinity conditions.

In preferred embodiments, SLP concentration in the topical cosmetic composition ranges from 0.001% to 90% of the total composition by weight, from 0.01% to 50%, from 0.05% to 10%, and preferably from 0.1% to 2.0%. In one embodiment, the topical composition comprises SLP in acidic form.

RLPs are glycolipids produced mainly by *Pseudomonas* bacteria. They are natural emulsifiers, and can be used according to the subject invention to replace non-biological surfactants, such as sodium lauryl sulfate, sodium dodecyl sulfate and sodium laureth sulfate, in a cosmetic composition. Furthermore, RLPs can be formulated to increase moisture retention or to lubricate skin, minimize the appearance of wrinkles, and increase smoothness of skin. Even further, RLPs can be used as antibacterial (Gram-positive) and antifungal agents.

In preferred embodiments, RLP concentration in the topical cosmetic composition ranges from 0.001% to 90% of the total composition by weight, from 0.01% to 50%, from 0.05% to 10%, and preferably from 0.1% to 2.0%.

Trehalose lipids (TLs) are glycolipids produced by, for example, the bacteria *Rhodococcus erythropolis*. TLs possess emulsifying and dispersing characteristics. They exhibit increased levels of surface activity and have certain antiviral and antimicrobial properties.

In preferred embodiments, TL concentration in the topical cosmetic composition ranges from 0.001% to 90% of the total composition by weight, from 0.01% to 50%, from 0.05% to 10%, and preferably from 0.1% to 2.0%.

Surfactin is a lipopeptide produced by certain bacterial strains, mainly *Bacillus subtilis*. Surfactin has high level surface activating function, and is extremely hydrophilic, forming a transparent gel at a wider range of concentrations than other biosurfactants. This biosurfactant can act as a skin penetration agent for cosmetic products, a foaming agent and an emulsifier. Furthermore, surfactin exhibits effective antibacterial (Gram-negative), antifungal and antiviral properties.

In preferred embodiments, surfactin concentration in the topical cosmetic composition ranges from 0.001% to 90% of the total composition by weight, from 0.01% to 50%, from 0.05% to 10%, from 0.1% to 5.0%, and preferably from 0.01% to 2.0%.

Additional biological amphiphilic molecules useful according to the present invention include mannoprotein, beta-glucan and other metabolites that have bio-emulsifying and surface/interfacial tension-reducing properties.

In some embodiments, the microbial growth by-products in the topical cosmetic composition can comprise therapeutically effective amounts of enzymes and/or proteins produced by microorganisms. For example, from about 0.001% to about 20% by weight, preferably from about 0.01% to about 15% by weight, or from about 0.05% to about 10% by weight, of one or more enzymes and/or proteins can be included. These can include, but are not limited to, exo-beta-1,3-glucanase, chitinase, esterases, lipases, glycosidases, amylases, and proteases beneficial for improving skin, scalp and/or hair health.

In some embodiments, the topical cosmetic composition further comprises therapeutically effective amounts of a skin-active agent, phosphatidylglycerol. In certain embodiments, the amount of phosphatidylglycerol is about 0.01 g/L to about 0.5 g/L, or about 0.05 g/L to about 0.75 g/L, or about 0.1 g/L to about 1.0 g/L.

Phosphatidylglycerol is a glycerophospholipid precursor to cardiolipin, a constituent molecule of the mitochondrial inner membrane. Cardiolipin is essential for the optimal function of numerous enzymes involved in mitochondrial energy metabolism. Supplementation of skin with cardiolipin and/or its precursor molecule(s) can enhance healing and/or repair of damaged skin, as well as restore aging skin to promote a more youthful appearance by, for example, supporting epithelial cell function.

In some embodiments, the topical cosmetic composition further comprises therapeutically effective amounts of a skin-active agent, resveratrol. In certain embodiments, the amount of resveratrol with respect to total weight of the subject topical composition ranges from 0.001 to 5.0% by weight, more preferably from 0.05 to 2.0% by weight, and most preferably from 0.2 to 1.0% by weight.

Resveratrol is a naturally-occurring substance found in the skin of fruits such as grapes, blueberries, raspberries and mulberries. It is reported to be an extremely potent antioxidant, a modulator of genetic expression via signal transduction, an inhibitor of inflammatory mediators and, by acting on diverse mechanisms simultaneously, it has been emphasized as a promising, multi-target, anticancer agent, relevant in both cancer prevention and treatment. Additionally, resveratrol has unique skin bleaching abilities, as it reduces the synthesis of melanin.

In one embodiment, the topical cosmetic composition can further comprise a polymeric stabilizer, such as, for example, from about 0.01% to about 5.0%, or from about 0.05% to about 2.0%, or from about 0.5% to about 1.0% poly(acrylic) acid. Poly(acrylic) acid helps to prevent resveratrol from crystallizing.

In some embodiments, the topical composition further comprises therapeutically effective amounts of a skin-active agent, hyaluronic acid. Hyaluronic acid is produced naturally in the fibroblasts of human skin, and can be used in the healing of skin wounds such as burns and ulcers, and as a skin moisturizer. Hyaluronic acid can aide in moisture retention, tissue repair, and holding together the collagen and elastin that make up the structural components of skin. It can also help create a protective barrier against undesirable microorganisms.

In one embodiment, the topical composition comprises from about 0.01% to about 10.0%, or from about 0.05% to about 8.0%, from about 0.5% to about 5.0%, or from about 1.0% to about 3.0% by weight hyaluronic acid.

In some embodiments, the topical cosmetic composition can further comprise a topically or cosmetically acceptable vehicle.

The cosmetically acceptable vehicle may be in the form of an emulsion. Non-limiting examples of suitable emulsions include water-in-oil emulsions, oil-in-water emulsions, silicone-in-water emulsions, water-in-silicone emulsions, wax-in-water emulsions, water-oil-water triple emulsions or the like having the appearance of a cream, gel or microemulsions.

As used herein, the term "oil" includes silicone oils unless otherwise indicated. The emulsion may include an emulsifier, such as a nonionic, anionic or amphoteric surfactant, or a gallant, typically in an amount from about 0.001% to about 5% by weight.

The cosmetically acceptable vehicle may include water; vegetable oils; mineral oils; ester oils such as octal palmitate, isopropyl myristate and isopropyl palmitate; ethers such as dicapryl ether and dimethyl isosorbide; alcohols such as ethanol and isopropanol; fatty alcohols such as cetyl alcohol, cetearyl alcohol, stearyl alcohol and behenyl alcohol; isoparaffins such as isooctane, isododecane (IDD) and isohexadecane; silicone oils such as cyclomethicone, dimethicone, dimethicone cross-polymer, polysiloxanes and their derivatives, preferably organomodified derivatives including PDMS, dimethicone copolyol, dimethiconols, and amodimethiconols; hydrocarbon oils such as mineral oil, petrolatum, isoeicosane and polyolefins, e.g., (hydrogenated) polyisobutene; polyols such as propylene glycol, glycerin, butylene glycol, pentylene glycol, hexylene glycol, caprylyl glycol; waxes such as beeswax, carnauba, ozokerite, microcrystalline wax, polyethylene wax, and botanical waxes; or any combinations or mixtures of the foregoing. Aqueous vehicles may include one or more solvents miscible with water, including lower alcohols, such as ethanol, isopropanol, and the like. The vehicle may comprise from about 1% to about 99% by weight of the composition, from 10% to about 85%, from 25% to 75%, or from 50% to about 65%.

In some embodiments, the topical cosmetic composition can further comprise additional cosmetic adjuvants and additives commonly included in cosmetic compositions, such as, for example, organic solvents, conditioners, stabilizers, silicones, thickeners, softeners, sunscreens, moisturizers or fragrances. The amounts of each ingredient, whether active or inactive, are those conventionally used in the cosmetic field to achieve their intended purpose, and typically range from about 0.0001% to about 25%, or from about 0.001% to about 20% of the composition, although the amounts may fall outside of these ranges. The nature of these ingredients and their amounts must be compatible with the production and function of the compositions of the disclosure.

In one embodiment, the composition may include additional skin actives, including but not limited to, retinoids, botanicals, keratolytic agents, desquamating agents, keratinocyte proliferation enhancers, collagenase inhibitors, elastase inhibitors, depigmenting agents, anti-inflammatory agents, steroids, anti-acne agents, antioxidants, and advanced glycation end-product (AGE) inhibitors, to name but a few.

In one embodiment, the composition may include additional anti-aging components, including, but not limited to, botanicals (e.g., *Butea frondosa* extract, *Aloe vera* extract); phytol; phytonic acid; phospholipids; silicones; petrolatum; triglycerides; omega fatty acids; retinoids; hydroxy acids (including alpha-hydroxy acids and beta-hydroxy acids), salicylic acid and alkyl salicylates; exfoliating agents (e.g., glycolic acid, 3,6,9-trioxaundecanedioic acid, etc.), estrogen synthetase stimulating compounds (e.g., caffeine and derivatives); compounds capable of inhibiting 5 alpha-reductase activity (e.g., linolenic acid, linoleic acid, finasteride, and mixtures thereof); and barrier function enhancing agents (e.g., ceramides, glycerides, cholesterol and its esters, alpha-hydroxy and omega-hydroxy fatty acids and esters thereof.)

Exemplary retinoids include, without limitation, retinoic acid (e.g., all-trans, or 9-cis, or 13-cis), and derivatives thereof, retinaldehyde, retinol (Vitamin A) and esters thereof, such as retinyl palmitate, retinyl acetate and retinyl propionate, and salts thereof. When present, the retinoids will typically be included in amounts from about 0.0001% to about 5% by weight, more typically from about 0.01% to about 2.5% by weight, or from about 0.1% to about 1.0% by weight. The composition an further comprise an antioxidant such as ascorbic acid and/or BHT; and/or a chelating agent such as EDTA or a salt thereof (e.g., disodium EDTA).

In another embodiment, the topical compositions of the present invention may also include one or more of the following: a skin penetration enhancer; an emollient, such as isopropyl myristate, petrolatum, volatile or non-volatile silicones oils (e.g., methicone, dimethicone), ester oils, mineral oils, and fatty acid esters; a humectant, such as glycerin, hexylene glycol or caprylyl glycol; a skin plumper, such as palmitoyl oligopeptide, collagen, collagen and/or glycosaminoglycan (GAG) enhancing agents; a sunscreen, such as avobenzone or octyl methoxycinnamate; an exfoliating agent; and an antioxidant.

Suitable exfoliating agents include, for example, alpha-hydroxy acids, beta-hydroxy acids, oxa-acids, oxadiacids, and their derivatives such as esters, anhydrides and salts thereof. Suitable hydroxy acids include, for example, glycolic acid, lactic acid, malic acid, tartaric acid, citric acid, 2-hydroxyalkanoic acid, mandelic acid, salicylic acid and derivatives thereof. One exemplary exfoliating agent is glycolic acid. When present, the exfoliating agent may comprise from about 0.001% to about 20% by weight of the composition.

Examples of antioxidants that may be used in the present compositions include compounds having phenolic hydroxy functions, such as ascorbic acid and its derivatives/esters; beta-carotene; catechins; curcumin; ferulic acid derivatives (e.g., ethyl ferulate, sodium ferulate); gallic acid derivatives (e.g., propyl gallate); lycopene; reductic acid; rosmarinic acid; tannic acid; tetrahydrocurcumin; tocopherol and its derivatives, including tocopheryl acetate; uric acid; or any mixtures thereof. Other suitable antioxidants are those that have one or more thiol functions (—SH), in either reduced or non-reduced form, such as glutathione, lipoic acid, thioglycolic acid, and other sulfhydryl compounds. The antioxidant may be inorganic, such as bisulfites, metabisulfites, sulfites, or other inorganic salts and acids containing sulfur. Antioxidants may comprise, individually or collectively, from about 0.001% to about 10% (w/w), or from about 0.01% to about 5% (w/w) of the total weight of the composition.

Non-biological surfactants can also be added to the formulation. Examples of surfactants include, but are not limited to, alkyl sulfates, alkyl ether sulfates (e.g., sodium/ammonium lauryl sulfates and sodium/ammonium laureth sulfates), amphoterics (e.g., amphoacetates and amphopropionates), sulfosuccinates, alkyl polyglucosides, betaines (e.g., cocamidopropul betaine (CAPB)), sultaines, sacrosinates, isethionates, taurates, ethoxylated sorbitan esters, alkanolamides and amino-acid based surfactants.

Viscosity modifiers can also be added to the compositions, including, for example, cocamide DEA, oleamide DEA, sodium chloride, cellulosic polymers, polyacrylates, ethoxylated esters, alcohol, glycols, xylene sulfonates, polysorbate 20, alkanolamides, and cellulose derivatives (e.g., hydroxypropyl methylcellulose and hydroxyethyl cellulose).

Polymers can also be added, include, for example, xanthan gum guar gum, polyquaternium-10, PEG-120 methyl glucose dioleate, PEG-150 distearate, PEG-150 polyglyceryl-2 tristearate and PEG-150 pentaerythrityl tetrastearate Other additives include: vitamins, such as tocopherol and ascorbic acid; vitamin derivatives such as ascorbyl monopalmitate, tocopheryl acetate, and Vitamin E palmitate; thickeners such as hydroxyalkyl cellulose, carboxymethylcellulose, carbombers, and vegetable gums such as xanthan gum; gelling agents, such as ester-terminated polyester amides; structuring agents; pigments, colorants or dyes; proteins, such as lactoferrin; and pH adjusters (citric acid, ethanolamine, sodium hydroxide, etc.).

The composition may optionally comprise other components known to those skilled in the art including, but not limited to, minerals, viscosity and/or rheology modifiers, skin cooling compounds, skin protectants, lubricants, fragrances, preservatives, stabilizers, pearls, chromalites, micas, preservatives, conditioners, anesthetics, anti-allergenics, antifungals, antimicrobials, anti-inflammatory agents, antiseptics, depigmenting agents, film formers, pharmaceutical agents, photostabilizing agents, surface smoothers, and optical diffusers.

In addition to the foregoing, the cosmetic compositions of the invention may contain any other compound for the improvement of skin, hair and/or scalp health and/or appearance. Details with respect to these and other suitable cosmetic ingredients can be found in the "International Cosmetic Ingredient Dictionary and Handbook," 10th Edition (2004), published by the Cosmetic, Toiletry, and Fragrance Association (CTFA), at pp. 2177-2299, which is herein incorporated by reference in its entirety. The amounts of these various substances are those that are conventionally used in the cosmetic or pharmaceutical fields, for example, they can constitute from about 0.01% to about 20% of the total weight of the composition.

The composition can be formulated within a wide range of pH levels. In one embodiment, the pH of the topical composition ranges from 1.0 to 13.0. In some embodiments, the pH of the topical composition ranges from 2.0 to 12.0. Other pH ranges suitable for the subject composition include from 3.5 to 7.0, or from 7.0 to 10.5. Suitable pH adjusters such as sodium hydroxide, citric acid and triethanolamine may be added to bring the pH within the desired range.

In some embodiments, the subject invention provides kits for at-home preparation and use of the subject compositions.
Growth of Microbes and Production of Microbial Growth by-Products The subject invention provides methods for cultivating microorganisms and production of microbial metabolites and/or other by-products of microbial growth. The microbial cultivation systems would typically use submerged culture fermentation; however, surface culture and hybrid systems can also be used. As used herein "fermentation" refers to growth of cells under controlled conditions. The growth could be aerobic or anaerobic.

In one embodiment, the subject invention provides materials and methods for the production of biomass (e.g., viable cellular material), extracellular metabolites (e.g. small molecules and excreted proteins), residual nutrients and/or intracellular components (e.g. enzymes and other proteins).

The microbe growth vessel used according to the subject invention can be any fermenter or cultivation reactor for industrial use. In one embodiment, the vessel may have functional controls/sensors or may be connected to functional controls/sensors to measure important factors in the cultivation process, such as pH, oxygen, pressure, temperature, agitator shaft power, humidity, viscosity and/or microbial density and/or metabolite concentration.

In a further embodiment, the vessel may also be able to monitor the growth of microorganisms inside the vessel (e.g., measurement of cell number and growth phases). Alternatively, a daily sample may be taken from the vessel and subjected to enumeration by techniques known in the art, such as dilution plating technique. Dilution plating is a simple technique used to estimate the number of microbes in a sample. The technique can also provide an index by which different environments or treatments can be compared.

In one embodiment, the method includes supplementing the cultivation with a nitrogen source. The nitrogen source can be, for example, potassium nitrate, ammonium nitrate ammonium sulfate, ammonium phosphate, ammonia, urea, and/or ammonium chloride. These nitrogen sources may be used independently or in a combination of two or more.

The method can provide oxygenation to the growing culture. One embodiment utilizes slow motion of air to remove low-oxygen containing air and introduce oxygenated air. The oxygenated air may be ambient air supplemented daily through mechanisms including impellers for mechanical agitation of the liquid, and air spargers for supplying bubbles of gas to the liquid for dissolution of oxygen into the liquid.

The method can further comprise supplementing the cultivation with a carbon source. The carbon source is typically a carbohydrate, such as glucose, sucrose, lactose, fructose, trehalose, mannose, mannitol, and/or maltose; organic acids such as acetic acid, fumaric acid, citric acid, propionic acid, malic acid, malonic acid, and/or pyruvic acid; alcohols such as ethanol, propanol, butanol, pentanol, hexanol, isobutanol, and/or glycerol; fats and oils such as soybean oil, rice bran oil, olive oil, corn oil, sesame oil, and/or linseed oil; etc. These carbon sources may be used independently or in a combination of two or more.

In one embodiment, growth factors and trace nutrients for microorganisms are included in the medium. This is particularly preferred when growing microbes that are incapable of producing all of the vitamins they require. Inorganic nutrients, including trace elements such as iron, zinc, copper, manganese, molybdenum and/or cobalt may also be included in the medium. Furthermore, sources of vitamins, essential amino acids, and microelements can be included, for example, in the form of flours or meals, such as corn flour, or in the form of extracts, such as yeast extract, potato extract, beef extract, soybean extract, banana peel extract, and the like, or in purified forms. Amino acids such as, for example, those useful for biosynthesis of proteins, can also be included.

In one embodiment, inorganic salts may also be included. Usable inorganic salts can be potassium dihydrogen phosphate, dipotassium hydrogen phosphate, disodium hydrogen phosphate, magnesium sulfate, magnesium chloride, iron sulfate, iron chloride, manganese sulfate, manganese chloride, zinc sulfate, lead chloride, copper sulfate, calcium chloride, calcium carbonate, and/or sodium carbonate. These inorganic salts may be used independently or in a combination of two or more.

In some embodiments, the method for cultivation may further comprise adding additional acids and/or antimicrobials in the liquid medium before and/or during the cultivation process. Antimicrobial agents or antibiotics are used for protecting the culture against contamination. Additionally, antifoaming agents may also be added to prevent the formation and/or accumulation of foam when gas is produced during cultivation.

The pH of the mixture should be suitable for the microorganism of interest. Buffers, and pH regulators, such as carbonates and phosphates, may be used to stabilize pH near a preferred value. When metal ions are present in high concentrations, use of a chelating agent in the liquid medium may be necessary.

The method and equipment for cultivation of microorganisms and production of the microbial by-products can be performed in a batch, quasi-continuous, or continuous processes.

In one embodiment, the method for cultivation of microorganisms is carried out at about 5° to about 100° C., preferably, 15 to 60° C., more preferably, 25 to 50° C. In a further embodiment, the cultivation may be carried out continuously at a constant temperature. In another embodiment, the cultivation may be subject to changing temperatures.

In one embodiment, the equipment used in the method and cultivation process is sterile. The cultivation equipment such as the reactor/vessel may be separated from, but connected to, a sterilizing unit, e.g., an autoclave. The cultivation equipment may also have a sterilizing unit that sterilizes in situ before starting the inoculation. Air can be sterilized by methods know in the art. For example, the ambient air can pass through at least one filter before being introduced into the vessel. In other embodiments, the medium may be pasteurized or, optionally, no heat at all added, where the use of low water activity and low pH may be exploited to control bacterial growth.

In one embodiment, the subject invention provides methods of producing a microbial growth by-product (e.g., a biosurfactant, enzyme, protein and/or other metabolite) by cultivating a microbe strain of the subject invention under conditions appropriate for growth and by-product production; and, optionally, purifying the growth by-product.

In one embodiment, the subject invention further provides a method for producing other microbial metabolites such as ethanol, lactic acid, beta-glucan, peptides, metabolic intermediates, polyunsaturated fatty acid, and lipids. The metabolite content produced by the method can be, for example, at least 20%, 30%, 40%, 50%, 60%, 70%, 80%, or 90%.

The biomass content of the fermentation broth may be, for example from 5 g/l to 180 g/l or more. In one embodiment, the solids content of the broth is from 10 g/l to 150 g/l.

The microbial growth by-product produced by microorganisms of interest may be retained in the microorganisms or secreted into the liquid medium.

In some embodiments, the growth by-product is kept in its crude form, without purification. This crude growth by-product can take the form of a liquid mixture comprising the growth by-product and fermentation broth. This crude form solution can comprise from about 25% to about 75%, from about 30% to about 70%, from about 35% to about 65%, from about 40% to about 60%, from about 45% to about 55%, or about 50% pure growth by-product.

In another embodiment, the method for producing microbial growth by-product may further comprise steps of concentrating and purifying the microbial growth by-product of interest. In a further embodiment, the liquid medium may contain compounds that stabilize the activity of microbial growth by-product.

In one embodiment, all of the microbial cultivation composition is removed upon the completion of the cultivation (e.g., upon, for example, achieving a desired cell density, or density of a specified metabolite in the broth). In this batch procedure, an entirely new batch is initiated upon harvesting of the first batch.

In another embodiment, only a portion of the fermentation product is removed at any one time. In this embodiment, biomass with viable cells remains in the vessel as an inoculant for a new cultivation batch. The composition that is removed can be a cell-free broth or contain cells. In this manner, a quasi-continuous system is created.

Advantageously, the method does not require complicated equipment or high energy consumption. The microorganisms of interest can be cultivated at small or large scale on site and utilized, even being still-mixed with their media. Similarly, the microbial metabolites can also be produced at large quantities at the site of need.

Preparation of Microbe-Based Products

One microbe-based product of the subject invention is simply the fermentation broth containing the microorganism and/or the microbial metabolites produced by the microorganism and/or any residual nutrients. The product of fermentation may be used directly without extraction or purification.

However, extraction and purification can be easily achieved using standard extraction and/or purification methods or techniques described in the literature. For example, in certain embodiments, the microbe-based product comprises simply the by-products of microbial growth, either in crude or purified form. In particular embodiments, the by-products are biosurfactants produced by the microorganisms grown according to the subject invention.

The microbes and/or broth resulting from the microbial growth can be removed from the growth vessel and transferred via, for example, piping for immediate use.

In other embodiments, the composition (microbes, broth, or microbes and broth) can be placed in containers of appropriate size, taking into consideration, for example, the intended use, the contemplated method of application, the size of the fermentation tank, and any mode of transportation from microbe growth facility to the location of use. Thus, the containers into which the microbe-based composition is placed may be, for example, from 1 gallon to 1,000 gallons or more. In other embodiments the containers are 2 gallons, 5 gallons, 25 gallons, or larger.

In certain embodiments, the compositions of the subject invention have advantages over, for example, biosurfactants alone, including one or more of the following: high concentrations of mannoprotein as a part of yeast cell wall's outer surface (mannoprotein is a highly effective bioemulsifier); the presence of biopolymer beta-glucan (another emulsifier) in yeast cell walls; the presence of biosurfactants in the culture, which are capable of reducing both surface and interfacial tension; and the presence of other metabolites (e.g., lactic acid, ethanol, etc.).

Upon harvesting the microbe-based composition from the growth vessels, further components can be added as the harvested product is placed into containers and/or piped (or otherwise transported for use). The additives can be, for example, buffers, carriers, other microbe-based compositions produced at the same or different facility, viscosity modifiers, preservatives, nutrients for microbe growth, tracking agents, solvents, biocides, other microbes and other ingredients specific for an intended use.

Other suitable additives, which may be contained in the formulations according to the invention, include substances that are customarily used for such preparations. Example of such additives include surfactants, emulsifying agents, lubricants, buffering agents, solubility controlling agents, pH adjusting agents, preservatives, stabilizers and ultra-violet light resistant agents.

In one embodiment, the composition may further comprise buffering agents including organic and amino acids or their salts. Suitable buffers include citrate, gluconate, tartarate, malate, acetate, lactate, oxalate, aspartate, malonate, glucoheptonate, pyruvate, galactarate, glucarate, tartronate, glutamate, glycine, lysine, glutamine, methionine, cysteine, arginine and a mixture thereof. Phosphoric and phosphorous acids or their salts may also be used. Synthetic buffers are suitable to be used but it is preferable to use natural buffers such as organic and amino acids or their salts listed above.

In a further embodiment, pH adjusting agents include potassium hydroxide, ammonium hydroxide, potassium carbonate or bicarbonate, hydrochloric acid, nitric acid, sulfuric acid or a mixture thereof.

In one embodiment, additional components such as an aqueous preparation of a salt as polyprotic acid such as sodium bicarbonate or carbonate, sodium sulfate, sodium phosphate, sodium biphosphate, can be included in the formulation.

Advantageously, in accordance with the subject invention, the microbe-based product may comprise broth in which the microbes were grown. The product may be, for example, at least, by weight, 1%, 5%, 10%, 25%, 50%, 75%, or 100% broth. The amount of biomass in the product, by weight, may be, for example, anywhere from 0% to 100% inclusive of all percentages therebetween.

Optionally, the product can be stored prior to use. The storage time is preferably short. Thus, the storage time may be less than 60 days, 45 days, 30 days, 20 days, 15 days, 10 days, 7 days, 5 days, 3 days, 2 days, 1 day, or 12 hours. In a preferred embodiment, if live cells are present in the product, the product is stored at a cool temperature such as, for example, less than 20° C., 15° C., 10° C., or 5° C. On the other hand, a biosurfactant composition can typically be stored at ambient temperatures.

In one embodiment, microbe strains are cultured for the purpose of producing an inactive (non-living) microbe-based composition. The composition is prepared by cultivating the desired microorganism, destroying the microbe by micro-fluidizing or gamma radiation (or by any other method known in the art not to cause protein denaturation), and then pasteurizing at lower temperatures. In one embodiment, inactivation occurs at pasteurization temperature (up to 65° to 70° C. for a time period sufficient to inactivate 100% of the yeast cells) and increasing pH value up to about 10.0. This induces partial hydrolysis of cells, destroys DNA, yet leaves valuable components, such as proteins and acids, intact. Then, the composition is neutralized to a pH of about 7.0-7.5 and the various components of hydrolysis are mixed.

Methods of Improving Facial Skin, Scalp and Hair Health and/or Appearance

The subject invention provides methods for improving a subject's facial skin, scalp and/or hair health utilizing microbe-based products. More specifically, the methods utilize the topical cosmetic compositions of the subject invention to improve a subject's facial skin, scalp and/or hair health and/or appearance.

The yeast cells utilized according to the subject methods can be, for example, *Pichia* yeasts or another biochemical-producing yeast (e.g., *Starmerella, Pseudozyma* or *Wickerhamomyces*). Additionally, when producing a mask composition according to the subject invention, further ingredients or suitable additives and/or adjuvants can be added to the composition, for example, a microbial biosurfactant or a skin-active agent.

In certain embodiments, methods are provided for improving skin, hair and scalp health, the methods comprising applying an effective amount of a topical cosmetic composition of the subject invention directly to the skin, hair and/or scalp for a number of minutes (e.g., 10 minutes) over a certain period of time (e.g., 1 month to 1 year or longer) sufficient to achieve a desired amount of improvement in health and/or appearance of skin, hair or scalp.

The composition can be applied using the fingers or hands or fingers, a comb, a paintbrush, a spatula, a cloth, a sponge, a cotton ball or round, or using any other tool or method known in the cosmetic arts. Preferably, care is taken to avoid applying the mask composition to the subject's eyelids, the skin surrounding the eyes, or the lips.

In certain embodiments, methods are provided for improving the health and/or appearance of a subject's facial skin, the methods comprising:
  a) cleaning the subject's facial skin using a non-medicated cleanser to remove makeup, dirt and oil from the skin;
  b) producing a facial mask composition comprising yeast cells and/or growth by-products thereof;
  c) applying a thin layer of the facial mask composition to the facial skin;
  d) allowing the facial mask composition to dry on the skin for a number of minutes; and
  e) washing away the facial mask composition using warm water.

Preferably, the step b) occurs immediately prior to step c). According to this embodiment, "immediately prior to" means 5 minutes or less, preferably, 4, 3 or 2 minutes or less, even more preferably, 1 minute or less beforehand.

In some embodiments, step b) can comprise adding yeast cells to a plant-based oil such as coconut oil or olive oil and mixing with water to form a thick paste. For example, in one embodiment, step b) can comprise mixing approximately 30-50 g of yeast cells with a natural oil, such as olive oil or coconut oil.

In certain embodiments, step b) further comprises mixing one or more skin-active agents with the facial mask composition, such as, for example, phosphatidylglycerol, hyaluronic acid, resveratrol, and/or an anti-comedo agent.

In one embodiment, step d) comprises allowing the facial mask composition to dry on the skin for 10 to 15 or 20 minutes.

In some embodiments, a subject can steam his or her face to relax the pores of the skin prior to applying a facial mask composition. Steaming can be achieved by any known and safe means, for example, by pouring boiling water into a bowl and placing the face over the bowl to allow the steam to contact the facial skin.

In some specific embodiments, the method comprises:
  a) cleaning the subject's facial skin using a non-medicated cleanser to remove makeup, dirt and oil from the skin;
  b) producing a peel-off facial mask composition comprising yeast cells and/or growth by-products thereof;
  c) applying a thin layer of the facial mask composition to the facial skin;
  d) allowing the facial mask composition to dry on the skin for a number of minutes, forming a compact film;
  e) peeling the film from the skin; and
  f) washing away any remaining film on the skin using warm water, wherein step b) comprises adding yeast cells to a powder mixture comprising sodium alginate, xanthan gum, calcium sulfate dihydrate, sorbitol, magnesium oxide, guar gum, diatomaceous earth, and tetrasodium pyrophosphate to form a yeast-powder mixture; and mixing the yeast-powder mixture with water and/or a plant-based oil at a ratio of, for example, about 1:25 to create a liquid or semi-liquid facial mask composition.

In certain embodiments, step b) further comprises mixing one or more skin-active agents with the facial mask composition, such as, for example, phosphatidylglycerol, hyaluronic acid, resveratrol, and/or an anti-comedo agent.

Preferably, the step b) occurs immediately prior to step c). According to this embodiment, "immediately prior to" means 5 minutes or less, preferably, 4, 3 or 2 minutes or less, even more preferably, 1 minute or less beforehand.

In one embodiment, step d) comprises allowing the facial mask composition to dry on the skin for 10 to 15 or 20 minutes In certain embodiments, the methods for improving the health and/or appearance of a subject's facial skin are applied until a desired improvement, replenishment, rejuvenation, moisturization and/or protection of the facial skin is achieved, for example, until one or more of the following benefits is achieved: more even skin tone, more radiant skin appearance, softer skin, reduction in redness, reduction in wrinkles, and/or reduction in pore size. The method can further be used for treating a skin condition, for example, acne vulgaris and/or others described herein.

In certain embodiments, the subject invention provides methods for improving hair and scalp health, the method comprising: a) mixing approximately 30-50 g of yeast cells with a natural oil, such as olive oil or coconut oil, to form a yeast-oil mixture; b) adding water to the yeast-oil mixture to form a thick paste; c) applying the paste to a subject's dry hair and scalp; d) covering the subject's hair with plastic wrap; e) allowing the paste to sit on the hair and scalp for at least one hour; and f) rinsing the paste from the hair and scalp. Optionally, the method can further comprise drying, and/or styling the hair in any fashion.

Steps a) and/or b) can further comprise adding other ingredients or suitable additives and/or adjuvants to the composition, for example, a microbial biosurfactant, a skin-active agent and/or a hair conditioning agent.

In certain embodiments, the topical cosmetic composition may be applied for a number of minutes per day, a number of repetitions per day, and for a number of days sufficient to achieve a desired improvement in skin, hair and/or scalp health and/or appearance.

The methods can further be used for treating a scalp condition, for example, dandruff or alopecia. For such uses, the topical composition is applied directly to an area of the skin where such a condition exists for a number of minutes per day, a number of repetitions per day, and for a number of days sufficient to achieve a reduction in the appearance of a condition and its related symptoms.

In order to achieve and/or maintain a desired effect, the methods for improving skin, hair and/or scalp health can be continued for as long as the effect is desired, e.g., until a condition has been diminished or eradicated, or until a positive change to the skin has been achieved. This may entail topical application at least once daily for at least one week, at least two weeks, at least four weeks, or at least eight weeks or more. In some embodiments, the composition is applied once every other day, once every two days, once every three days, once per week, etc., for a period of one or more weeks. Once the application of the topical composition is discontinued, the desired improvement in the health of the skin, scalp or hair may also diminish.

In addition the face, scalp and hair, the subject compositions and methods are also suitable for use on any part of a subject's skin, i.e., integument. Such locations can include, but are not limited to, the skin of the ears, neck, back, shoulders, arms, hands, chest, abdomen, buttocks, legs and feet.

In one embodiment, the compositions of the invention will be applied in an amount from about 0.001 to about 100 mg/cm$^2$, more typically from about 0.01 to about 20 mg/cm$^2$, or from about 0.1 to about 10 mg/cm$^2$.

EXAMPLES

It should be understood that the examples and embodiments described herein are for illustrative purposes only and that various modifications or changes in light thereof will be suggested to persons skilled in the art and are to be included within the spirit and purview of this application.

Example 1—Kits

In some embodiments, the subject invention provides kits for convenient at-home preparation and use of the subject topical cosmetic microbe-based compositions.

The kits can comprise a box or other package to house all components for preparing and applying one application of the face or hair masks, as well as instructions for the same.

The box can house individual pre-measured packages for each of the components used in forming the mask composition. One sealed package would comprise the yeast cells and/or their growth by-products. This might be in a liquid form, for example, comprising fermentation broth in which the yeast cells were cultivated. This might also be in a dried form.

In the case of a peel-off facial mask, a second sealed package can contain a powder mixture comprising sodium alginate, xanthan gum, calcium sulfate dihydrate, sorbitol, magnesium oxide, guar gum, diatomaceous earth, and/or tetrasodium pyrophosphate. Optionally, another sealed package could contain further skin-active agents and/or cosmetically-acceptable additives, for example a biosurfactant composition and/or phosphatidylglycerol, although these components could also be in the powder mixture of the second sealed package.

In the case of a hair mask, a sealed bottle or container can comprise, e.g., olive oil or coconut oil. A third sealed package can contain yeast extract and optionally, cosmetically-acceptable additives, for example a biosurfactant composition. The kit can also comprise a natural hair colorant and/or a comb.

The kit can further comprise a container or a bowl for mixing the different components of the compositions together. It is envisioned that water would be obtained from a tap source. The kit can further comprise a tool for mixing. The mixing tool can be multipurpose, meaning it can also be used for applying the composition to a subject's face, hair or scalp; however, a separate tool can be included for applying the composition, though the hands can also be used. The kit can further comprise gloves to keep the hands clean (if desired).

The kits can be used to practice the methods of the subject invention. For example, a kit can be used to prepare a topical cosmetic composition, either in the form of a face mask or a hair mask, which can then be immediately applied to a subject's face, hair or scalp according to the subject methods.

Example 2—Cultivation of *Pichia* Yeast for Enzyme Production and Use in Personal Care Compositions

*Pichia* yeasts can be used to produce a variety of personal care compositions, as their cell derivatives can eliminate fungus that contaminates the skin, reduce pathogenic yeasts growing on the skin and mucosal surfaces, decrease bacterial contamination of the skin and mucosa, and stimulate the production of collagen and elastin in skin cells (to name a few).

The basic cultivation medium for producing *Pichia anomala* (*Wickerhamomyces anomalus*), *Pichia kudriavzevii* and *Pichia guilliermondii* (*Meyerozyma guilliermondii*) is identical for all three species. The medium comprises 2% glucose, 1% yeast extract, 1% canola oil, 5% glycerol, and 50 mM citrate buffer. If *Pichia guilliermondii* is being cultivated for production of chitinase, 0.1% micronized chitin is added. If organic status is desired for the cosmetic product, no inorganic salts are used, and all nutrient medium components must be certified for the organic status.

The temperature for fermentation can range from 25-30° C., and initial pH can range from 5.5-6.0. Saturated oxygen can range from 15-25% (of 100% ambient air). Total fermentation time can be up to 72 hours (determined by reaching the stationary phase).

For production of concentrated enzymes and/or proteins, once a culture has been produced, it should immediately be cooled down to 5-10° C. to prevent possible degradation of active substances in the supernatant. Then the yeast biomass and yeast supernatant are isolated via centrifugation or microfiltration (or combination thereof) through a 0.1-micron filter while keeping the process at a temperature no higher than 10° C.

Protein molecules can be precipitated out with using a salting technique. The proteins are salted out by increasing concentration of salt, i.e., ammonium sulfate. After the proteins are concentrated 10-20 folds (or more, depending on the necessary concentration for the final personal care product), they are collected and washed out by a cold saline solution 2-3 times (with constant mixing for 1 hour each time).

Enzymatic activity of the concentrated product can be stabilized by mixing it with sodium alginate to a final concentration of 1% sodium alginate, or mixing it with xanthan gum to a final concentration of 0.5% of xanthan gum.

The antibacterial or antifungal activity of the final resulting substrate can be tested. Antifungal capabilities can be tested by well plate assays with *Candida* yeasts (of clinical significance) and *Malassezia* fungus, whereas for antibacterial activity, the cultures of *E. coli* and *P. aeruginosa* can be used. Growth inhibition should be measured using the diameter of inhibition in millimeters around the well.

Once testing has been conducted, the concentrated yeast by-products, as well as the leftover yeast biomass, can be used to produce a variety of personal care products.

Example 3—Cultivation of *Wickerhamomyces anomalus* and *Pseudozyma Aphidis* for Biosurfactant Production

*Wickerhamomyces anomalus* yeast is grown in a reactor with working volume of 800 L for biomass and biosurfactant production in non-sterilized conditions. A method of empty vessel sanitation is used wherein internal surfaces are treated with 2-3% hydrogen peroxide and rinsed with bleach and high pressure hot water. The culture medium components containing all necessary components are temperature decontaminated at 85-90° C. or dissolved in 3% hydrogen peroxide. The fermentation temperature is kept between 25-30° C. The pH begins at 5.0-5.5, and then decreases to 3.0-3.5, where it is stabilized. Production of biomass is achieved in about 48 hours of fermentation.

Accumulation of biosurfactants can occur after 7 to 9 days of fermentation. Upon completion of the fermentation, the culture containing biomass and, if applicable, low concentration of biosurfactants, both of which can be added to face and hair mask compositions.

*Pseudozyma aphidis* is grown in the same reactors under the same conditions, with two exceptions: optimal pH is kept between 5.0-5.5, and production of biomass and mannosylerythritol lipids (MELs) is achieved in 7 to 12 days. MELs can be included in the compositions of the subject invention.

Example 4—Fermentation of *Starmerella bombicola* for SLP Production and Purification Fermentation of *Starmerella bombicola* for SLP production was performed in a 14-liter reactor as a fed-batch fermentation in a nutrient medium containing 0.5% yeast extract, 10% glucose, 10% canola oil, 1% urea. The initial pH was 5.5. Temperature of cultivation was 25° C.

Initially, fermentation continued for 5 days and then resulting SLP was harvested. After adding additional amounts of the nutritional components into the reactor, keeping the same proportions, the process continued. Then, in 2-3 days, new portions of SLP were harvested.

The amount of SLP harvested from each cycle ranged from 0.5-1.0 liters of the final product. Concentration of SLP in the product typically reached 50%. This quasi-continuous technological process typically continued for 2 weeks, after which a new cycle would begin.

After SLP was harvested from the fermentation products, the SLP was purified by conducting filtration of 10% water solution through the filters with 2-micron pore size. The product can then be stored in a refrigerator for making the cosmetic composition.

We claim:

1. A composition for improving facial skin, scalp and/or hair health, the composition comprising a therapeutically effective amount of yeast cells, selected from *Pichia anomala* (*Wickerhamomyces anomalus*), *Pichia kudriavzevii* (*Wickerhamomyces kudriavzevii*), and *Pichia guilliermondii* (*Meyerozyma guilliermondii*).

2. The composition of claim 1, wherein the yeast cells are dried yeast cells.

3. The composition of claim 1, further comprising microbial growth by-products that are biological amphiphilic molecules, enzymes and/or proteins.

4. The composition of claim 3, wherein the biological amphiphilic molecules are biosurfactants selected from glycolipids and lipopeptides, wherein the glycolipids are selected from mannosylerythritol lipids (MELs), sophorolipids (SLPs), trehalose lipids (TLs) and rhamnolipids (RLPs); and wherein the lipopeptides are selected from surfactin, iturin, lichenysin and fengycin.

5. The composition of claim 3, wherein the enzymes and/or proteins are selected from exo-beta-1,3-glucanase, esterases, lipases, glycosidases, amylases, proteases, and chitinases.

6. The composition of claim 1, further comprising one or more of a plant-based oil, sodium alginate, xanthan gum, calcium sulfate dihydrate, sorbitol, magnesium oxide, guar gum, diatomaceous earth, tetrasodium pyrophosphate, water and/or a skin-active agent.

7. The composition of claim 1, formulated as a facial mask.

8. The composition of claim 7, comprising 30-50 g of said yeast cells and 50 to 300 ml of a plant-based oil.

9. The composition of claim 1, formulated as a hair mask.

10. The composition of claim 9, further comprising yeast extract.

11. The composition of claim 10, comprising 30-50 g of said yeast cells, 50 to 300 ml of olive oil or coconut oil, and 5 to 25 g of yeast extract.

12. The composition of claim 1, further comprising one or more cosmetic adjuvants and/or additives.

13. The composition of claim 12, wherein the adjuvants and/or additives are selected from organic solvents, silicones, pH adjusters, chelating agents, gelling agents, proteins, vitamins, emollients, oils, hydroxy acids, exfoliants, viscosity modifiers, polymers, minerals, insect repellents, lubricants, preservatives, botanicals, clarifying agents, non-biological surfactants, antioxidants, thickeners, softeners, sunscreens, moisturizers, colorants, and fragrances.

14. A method of improving a subject's facial skin health, the method comprising:
   a) cleaning the subject's facial skin using a non-medicated cleanser to remove makeup, dirt and oil from the skin;
   b) producing a facial mask composition comprising yeast cells;
   c) applying a thin layer of the facial mask composition to the facial skin;
   d) allowing the facial mask composition to dry on the skin; and
   e) washing away any part of the mask composition remaining on the skin using warm water,
   wherein said yeast cells are selected from *Pichia anomala* (*Wickerhamomyces anomalus*), *Pichia kudriavzevii* (*Wickerhamomyces kudriavzevii*), and *Pichia guilliermondii* (*Meyerozyma guilliermondii*).

15. The method of claim 14, wherein step b) further comprises adding one or more microbial growth by-products, one or more skin-active agents and/or one or more cosmetic additives and/or adjuvants to the composition.

16. The method of claim 15, wherein the microbial growth by-product is a microbial biosurfactant.

17. The method of claim 14, wherein step b) occurs 5 minutes or less before step c).

18. The method of claim 14, wherein b) comprises mixing 30-50 g of said yeast cells with 50-300 ml of coconut oil or olive oil.

19. The method of claim 14, wherein step b) comprises:
   adding said yeast cells to a powder mixture comprising sodium alginate, xanthan gum, calcium sulfate dihydrate, sorbitol, magnesium oxide, guar gum, diatomaceous earth, and tetrasodium pyrophosphate to form a yeast-powder mixture; and mixing the yeast-powder mixture with water at a ratio of about 1:25 to create a liquid or semi-liquid facial mask composition.

20. The method of claim 19, wherein d) comprises allowing the facial mask composition to dry on the skin, thereby forming a compact film, and wherein the method further comprises e) peeling the film from the skin.

21. The method of claim 14, wherein prior to applying the facial mask composition to the subject's facial skin, the method further comprises steaming the subject's face to relax the pores of the skin.

22. The method of claim 14, performed once or twice daily.

23. A method of improving a subject's scalp and hair health, the method comprising:
  a) mixing approximately 30-50 g of yeast cells with coconut oil or olive oil;
  b) adding water to the yeast-olive oil mixture to form a thick paste;
  c) applying the paste to a subject's dry hair and scalp;
  d) covering the subject's hair with plastic wrap;
  e) allowing the paste to sit on the hair and scalp for at least one hour; and
  f) rinsing the paste from the hair and scalp,
wherein said yeast cells are selected from *Pichia anomala* (*Wickerhamomyces anomalus*), *Pichia kudriavzevii* (*Wickerhamomyces kudriavzevii*), and *Pichia guilliermondii* (*Meyerozyma guilliermondii*).

24. The method of claim 23, wherein step b) further comprises adding one or more microbial growth by-products, one or more skin-active agents and/or one or more cosmetic additives and/or adjuvants to the composition.

25. The method of claim 23, wherein the composition is applied daily.

26. The method of claim 23, wherein the daily application is repeated for one week or longer.

27. The composition of claim 6, wherein the skin-active agent is phosphatidylglycerol, resveratrol, hyaluronic acid or an anti-comedo agent.

28. The composition of claim 27, comprising about 0.01 g/L to about 1.0 g/L of phosphatidylglycerol.

29. The method of claim 14, wherein the subject's facial skin is improved in one or more of the following manners: improved evenness of skin tone, reduced redness, reduced wrinkles, reduced pore size, increased radiance, and increased softness.

30. The method of claim 15, wherein the skin-active agent is phosphatidylglycerol, resveratrol, hyaluronic acid, or an anti-comedo agent.

31. The method of claim 24, wherein the microbial growth by-product is a microbial biosurfactant.

32. The method of claim 24, wherein the skin-active agent is phosphatidylglycerol, resveratrol, hyaluronic acid, or an anti-comedo agent.

* * * * *